United States Patent [19]
Biermann

[11] 3,946,228
[45] Mar. 23, 1976

[54] METHOD AND APPARATUS FOR DETERMINING GAS CONTENT IN INORGANIC SUBSTANCES

[75] Inventor: Rudolf Biermann, Erlangen, Germany

[73] Assignee: Siemens Aktiengesellschaft, Munich, Germany

[22] Filed: May 17, 1974

[21] Appl. No.: 470,972

[30] Foreign Application Priority Data
May 24, 1973 Germany.......................... 2326596

[52] U.S. Cl. ..................... 250/282; 250/288; 73/19
[51] Int. Cl.².......................................... G01M 7/14
[58] Field of Search ........ 250/288, 289, 282; 73/19; 23/230 PC, 253 PC

[56] References Cited
UNITED STATES PATENTS

| | | | |
|---|---|---|---|
| 2,995,922 | 8/1961 | Firth et al. | 73/19 |
| 3,498,105 | 3/1970 | Hetherington | 73/19 |
| 3,529,937 | 9/1970 | Ihara et al. | 23/230 PC |
| 3,559,453 | 2/1971 | Aspinal et al. | 73/19 |
| 3,844,716 | 10/1974 | Noakes | 23/230 PC |

*Primary Examiner*—James W. Lawrence
*Assistant Examiner*—B. C. Anderson
*Attorney, Agent, or Firm*—Kenyon & Kenyon Reilly Carr & Chapin

[57] ABSTRACT

A method and apparatus for determining the gas content of inorganic conductive and semiconductive elements and compounds having a low sublimation temperature, in which a melt of the substance in a crucible has a pressure approximately equal to the saturation vapor pressure maintained above the melt with a high vacuum maintained in the extraction chamber. In the disclosed embodiment, this is accomplished in a gas extraction system which can be evacuated and in which is contained a graphite crucible used as a sample vessel with means for heating the crucible by direct passage of current with the crucible having a conically fitted and drilled graphite cover into which a sintered filter is pressed for maintaining the pressure above the melt.

10 Claims, 2 Drawing Figures

METHOD AND APPARATUS FOR DETERMINING GAS CONTENT IN INORGANIC SUBSTANCES

BACKGROUND OF THE INVENTION

This invention relates to the measurement of the gas content in substances and more particularly to the measurement of such gas content in inorganic conductive and semiconductive elements and compounds having a low sublimation temperature.

The gas content in metals can be measured using the well known high-vacuum gas extraction method or through gas extraction in a protective gas also referred to as the carrier gas method. These methods and the apparatus developed in connection therewith are essentially limited to substances whose sublimation temperature is close to or above 1000°C, i.e., to high melting metals or their alloys. When using the high vacuum extraction method for example, and with a mass spectrometer as an analyzer, the material to be investigated is melted. The degassing temperature is short and sufficiently high to ensure an adequately high diffusion velocity of all components of interest in the melt, with the evaporation rate of the material being investigated low during the degassing. With this method, it is theoretically possible to detect qualitatively and quantitatively all the components given off by the sample using a single measurement. However, these criteria required for gas content determinations using this method are met only by materials having a sublimation temperature from 1000°C on up. The high vacuum extraction method is not suitable for substance having a low sublimation temperature such as those having sublimation temperature from 200°C on up. Furthermore, use of the carrier gas method for determination of the gas content in such substances is not possible since, at the necessary high temperature, the sublimation rate of the sample to be investigated is still too high.

Thus, it can be seen that there is a need for a method and apparatus which permits making reliable qualitative and quantitative measurements of the gas content in inorganic conductive and semiconductive elements and their compounds having a low sublimation temperature in a simple manner.

SUMMARY OF THE INVENTION

The present invention provides such a method and apparatus. The sample is placed in a sample vessel of graphite associated with which are means for heating by direct passage of current. That is, the graphite crucible is arranged between two moveable current supply electrodes in an extraction chamber which includes means for evacuation. In accordance with the present invention, the melt situated in the crucible has a pressure maintained above it which is equal to or approximately equal to the saturation pressure generated, with the extraction chamber evacuated and a high vacuum maintained therein. The method has been found extremely well suited for the determination of the $H_2$, $O_2$ and $N_2$ content of such materials, but may also be used for determining the presence and amounts of other gases and vapors. All components given off can be determined qualitatively and quantitatively in a single measurement. The method of the present invention has been found suitable for measuring the gas content of the elements arsenic, antimony, bismuth, selenium, tellurium and lead along with gallium arsenide, with which the prior art method using high vacuum gas extraction failed because of excessive evaporation rates of the substances and their getter action.

In the disclosed embodiment, the saturation vapor pressure is maintained by a filter designed so that the substance being measured cannot sublimate through the filter but that gas can be extracted therethrough for measurement. The filter is placed over the crucible and for that reason, the present method is referred to as the crucible-filter method. Filters which may be used for practicing the present invention have as an essential property, a semipermeable wall, i.e., the filter must be of a substance which is permeable for gas molecules and impermeable for the vapor particles of the substance being investigated. Surprisingly, it has been discovered that the filters of the present invention can be reused over and over again, without danger of clogging up for filters to a mean pore width of approximately 3 $\mu$m.

Particularly suitable filter materials are porous materials, such as quartz, ceramics, porous graphite or aluminum silicate. Furthermore, sintered metal filters such as sintered FeNi material were found to be suitable in certain cases. A particularly well suited filter material is sintered $SiO_2$ with a mean pore diameter of about 20 $\mu$m and an $Al_2O_3$ filter with a mean pore diameter of 3 to 5 $\mu$m.

In accordance with the method of the present invention, the substance to be investigated is placed in a graphite crucible which is covered by a conically fitted and drilled graphite filter. A sintered filter is pressed into the graphite cover. The covered crucible is placed in a highly evacuated vessel between two current supply electrodes and is heated by direct passage of current. The substance sublimates and the pressure in the crucible rises to a value which is approximately equal to the saturation vapor pressure of the substance.

In the apparatus of the present invention, the graphite crucible has a conically fitted and drilled graphite cover into which a sintered filter is pressed. Teflon rings are used for establishing a high vacuum resistant seal in the evacuation chamber.

DETAILED DESCRIPTION OF THE PREFERRED EMBODIMENT

Figure 1:
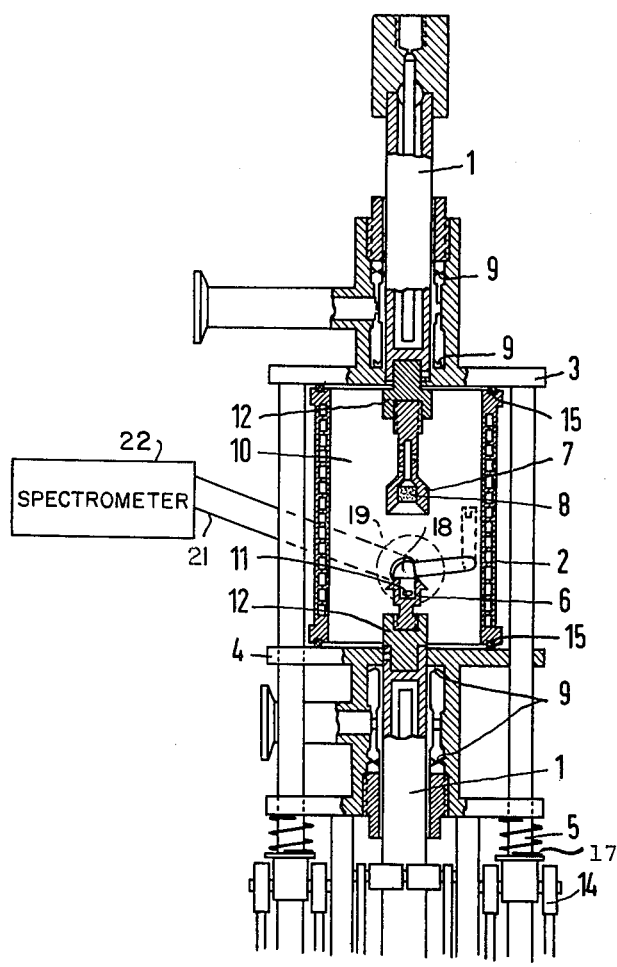
FIG. 1 is a cross sectional schematic view of an embodiment which may be used for carrying out the method of the present invention.

FIG. 1 illustrates an apparatus for carrying out the method of the present invention. On the figure, copper electrodes for supplying heating current to a crucible are designated 1, with one electrode provided at the bottom of the apparatus and another at the top. A steel enclosure 2 having an upper flange 3 and a lower flange 4, which is a double flange, define the evacuation chamber 10. The upper flange 3 holds and guides the upper electrode along with closing off the extraction chamber 10. It is mounted rigidly on four cylindrical rods 15 or V2A steel. A high vacuum resistant seal is established through the use of a teflon ring 15. The double flange 4 is provided with holes through which the cylindrical rods 15 pass so that it may slide thereon. Lifting rods 14 along with springs 17 are used to press the lower flange 4 against the lower sealing surface at which a teflon ring 15 is installed. Like the flange 3, the flange 4 also guides the electrodes. In conventional fashion, the copper electrodes 1 are water-cooled and sealed against the atmosphere and the extraction chamber using squeezed and sheared teflon rings.

In accordance with a further feature of the invention, intermediate molybdenum pieces 12 are provided containing internal threads, into which the graphite crucible 6 and the graphite cover 7 having a built-in sintered filter 8 can be screwed. These then comprise the end faces of the electrodes 1, at least the lower of which is moveable so that the graphite cover may be moved up to come in sealing contact with the graphite crucible 6. As is more clearly illustrated by FIG. 2, the sealing surface between the crucible and the cover is conical so that adequate tightness is insured even after the parts have been used several times. Suitable dimensions for the filter are 7.0 mm diameter and 6 mm height. The crucible has an inside diameter of 8 mm and a depth of 8 mm. The weight of the sample, designated 11 is approximately 0.1 to 0.1 g. In accordance with the present invention, the crucible 6 and cover 7 are brought together and heated by the direct passage of current through the crucible and cover.

This arrangement is particularly suited for determination of the gas content of inorganic, conducting and semiconducting elements and their compounds with a low sublimation temperature. In particular, in determining $H_2$, $O_2$ and $N_2$ in such substances, the arrangement was found to be insensitive to interference. It is easy to operate and results in short measuring times. The entire degassing time of the sample is only approximately 5 minutes. Furthermore, it is readiy movable and is small. The detection threshold is determined in each case by the uncharged reading of the apparatus. For $O_2$ and $N_2$ it is about $0.5 \times 10^{-4}$ percent by weight and for $H_2$ about $0.1 \times 10^{-4}$ percent by weight. A further advantage of the apparatus results in the fact that it can be connected directly with a device for determining the gases and vapors, such as a mass spectrometer. If a suitable analyzer is chosen, a single measurement can determine all the gaseous substances given off by the sample. Such a direct connection is shown. A bore 18 in the steel enclosure 2 is provided leading to an appropriate flange 19 to which is coupled the flange from a line 21 leading to a spectrometer or other conventional type of analyzer 22.

Referring again to FIG. 2, the sintered filter 8 which is pressed into the drilled graphite cover 7 is clearly shown. As illustrated, passages are provided above the filter 8 to permit the escape of the gaseous substances given off by the material in the crucible 6 so that they may be measured by a suitable analyzer.

Figure 2:
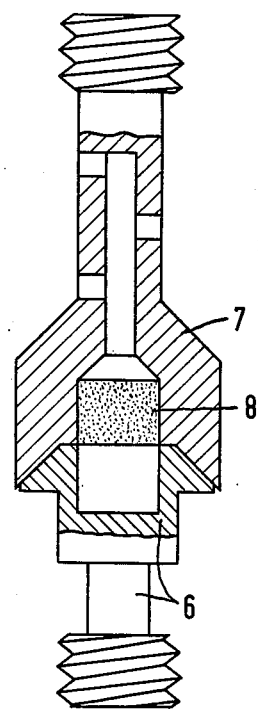
FIG. 2 is an enlarged cross section of the crucible of the present invention.

The following examples described measurements made using apparatus according to FIGS. 1 and 2.

EXAMPLE 1

Into the graphite crucible, 0.15 g of selenium was placed and heated to 1000°C using a current of 180A. The gases or vapors given off by the sample were analyzed and recorded using a directly coupled mass spectrometer (Varian MAT, Type CH5). The gas content determination resulted in readings of $23 \times 10^{-4}$ percent by weight of oxygen and $13 \times 10^{-4}$ percent by weight of nitrogen.

EXAMPLE 2

With the same arrangement as described in Example 1, the oxygen content of GaAs in a sample of 0.1 g was determined. The reading was $11 \times 10^{-4}$ percent by weight of oxygen in the GaAs sample.

EXAMPLE 3

Using an arrangement the same as that used in Examples 1 and 2, oxygen emission was measured for lead with and without surface oxidation. As samples, 0.26 g of surface-oxidized lead and 0.30 g of non-surface oxidized lead were used. The respective nitrogen and oxygen emissions for the oxidized sample were respectively $19 \times 10^{-4}$ percent by weight and $72 \times 10^{-4}$ percent by weight and for the non-oxidized sample $21 \times 10^{-4}$ percent by weight and $8.5 \times 10^{-4}$ percent by weight.

In each case, the correctness of the results obtained was subsequently checked using samples with known $O_2$ contents. The agreement of the values can be seen from the following Table.

TABLE

| Measurement | Substance | Oxygen Content (Emission $\times 10^{-4}$% by weight) | |
|---|---|---|---|
| | | by gas extraction with the crucible-filter method according to the invention | by activation analysis |
| 1 | Se (Fluka) | 10.7 | 10.5 – 11.2 |
| 2 | Se (Fluka) | 9.8 | 10.5 – 11.2 |
| 3 | Se (Fluka) | 10.1 | 10.5 – 11.2 |

It is evident from the above table that the values determined by the method of the present invention agree well with their results of similar measurements made by activation analysis.

Thus an improved method for determining the gas content of inorganic substances having a low sublimation temperature has been shown. Although specific method and apparatus for carrying out that method have been illustrated and described, it will be obvious to those skilled in the art that various modifications may be made without departing from the spirit of the invention which is intended to be limited solely by the appended claims.

What is claimed is:

1. A method for determining the gas content of inorganic, conducting and semiconducting elements and their compounds having a low sublimation temperature, by heating a sample vessel of graphite by direct passage of current, with the sample vessel arranged in an evacuated extraction chamber between two movable current supply electrodes, and analyzing the gas given off by a sample placed in the sample vessel by mass spectrometry wherein the improvement comprises generating and maintaining a pressure above the sample in the sample vessel which is approximately equal to the saturation vapor pressure of the substance being measured by placing a filter over said sample vessel while maintaining a high vacuum in the extraction chamber.

2. A method according to claim 1 wherein said filter comprises a porous material.

3. A method according to claim 2 wherein said filter comprises a material selected from the group consisting of quartz, graphite and sintered metal.

4. Apparatus for determining the gas content of inorganic, conducting and semiconducting elements and their compounds having a low sublimation temperature comprising:
   a. an extraction chamber;
   b. first and second movable electrodes extending into said chamber;
   c. a sample vessel of graphite;
   d. a conically fitted and drilled graphite cover for said sample vessel;
   e. a sintered filter pressed into said graphite vessel;
   f. mass spectrometer means coupled to said extraction chamber for the direct determination of gases and vapors and
   g. wherein said graphite vessel and cover are arranged between said current supply electrodes whereby by placing a sample in said vessel and passing a current therethrough gases contained in said sample will be emitted and can be measured by said means for direct determination.

5. Apparatus according to claim 4 wherein said evacuation chamber is sealed by a Teflon seal to thereby establish a high vacuum resistant seal.

6. Apparatus according to claim 4 wherein said electrodes comprise copper electrodes having intermediate molybdenum pieces on their end faces which molybdenum end faces contact the graphite sample vessel and graphite cover respectively.

7. Apparatus according to claim 5 wherein said electrodes comprise copper electrodes having intermediate molybdenum pieces on their end faces which molybdenum end faces contact the graphite sample vessel and graphite cover respectively.

8. Apparatus according to claim 6 wherein said molybdenum pieces contain internal threads and said graphite vessel and cover have, on their ends, matching threads whereby said vessel and cover may be screwed into said molybdenum pieces.

9. Apparatus according to claim 4 wherein said means for direct determination comprises means for the direct determination of $H_2$, $O_2$, $N_2$ and other gases and vapors.

10. Apparatus according to claim 8 wherein said means for direct determination comprise means for the direct determination of $H_2$, $O_2$, $N_2$ and other gases and vapors.

* * * * *